United States Patent [19]

Speiser

[11] 4,013,784
[45] Mar. 22, 1977

[54] DELAYED RELEASE PHARMACEUTICAL PREPARATIONS

[76] Inventor: Peter Speiser, Clausiusstr. 25, 8006 Zurich, Switzerland

[22] Filed: Oct. 2, 1974

[21] Appl. No.: 511,174

[30] Foreign Application Priority Data

Dec. 6, 1973 Germany .................... 2360796

[52] U.S. Cl. ............................................. 424/19
[51] Int. Cl.² ..................................... A61K 9/22
[58] Field of Search ............................. 424/19–22

[56] References Cited

UNITED STATES PATENTS

| 2,793,979 | 5/1957 | Svedres | 424/22 |
| 2,805,977 | 9/1957 | Robinson et al. | 424/19 |
| 2,875,130 | 2/1959 | Grass et al. | 424/19 |
| 2,987,445 | 6/1961 | Levesque | 424/22 |
| 3,062,720 | 11/1962 | Costello | 424/22 |
| 3,146,167 | 8/1964 | Lantz et al. | 424/19 |
| 3,400,197 | 9/1968 | Lippmann | 424/21 |
| 3,629,393 | 12/1971 | Nakamoto et al. | 424/22 |

OTHER PUBLICATIONS

C.A. 79 No. 27063r (1973).
C.A. 78 No. 47805s (1973); C.A. 73 No. 38547d (1970); C.A. 75 No. 674766 (1971).
C.A. 76 No. 37436s (1972); C.A. 60 No. 15686n (1964); C.A. 68 No. 11496w (1968); C.A. 76 No. 68234d (1972).
C.A. 77 No. 147956g (1972).

Primary Examiner—Shep K. Rose
Attorney, Agent, or Firm—Erich M. H. Radde

[57] ABSTRACT

A novel delayed release pharmaceutical preparation which is free of added enzymes and thus is stable on storage is provided. The preparation comprises particles of the therapeutically effective agent, a water-soluble calcium salt, and, if desired, a filler material, stabilizer, and other additives uniformly embedded in a triglyceride of fatty acids with 12 to 18 carbon atoms, thereby forming a granular preparation of a grain size between about 0.1 mm. and about 1.0 mm. A process of producing such a preparation is also disclosed.

10 Claims, No Drawings

DELAYED RELEASE PHARMACEUTICAL PREPARATIONS

BACKGROUND OF THE INVENTION

1. FIELD OF THE INVENTION

This invention relates to a delayed release pharmaceutical preparation and more particularly to a delayed or timed release pharmaceutical preparation for peroral administration. Such a preparation is intended to achieve the delayed release of pharmaceutically active agents in the intestinal tract.

2. DESCRIPTION OF THE PRIOR ART

Pharmaceutical formulations comprising a mixture of fatty acid triglycerides (principally trilaurin and tristearin), glyceryl monostearate, calcium carbonate, a pharmaceutically active agent, and lipase have already been tested with respect to the manner in which they release the active agent, by CH. W. HARTMAN (U.S. Pat. No. 3,493,652) and by K. A. JAVAIT and CH. W. HARTMAN in vitro and in vivo on dogs (J.Pharm.Sci. 60, 1709 (1971) and 61, 900 (1972)).

SUMMARY OF THE INVENTION

It is one object of the present invention to provide a highly effective, delayed or timed release pharmaceutical preparation for oral administration which causes delayed or timed release of pharmaceutically effective agents in the intestinal tract.

Another object of the present invention is to provide a simple and effective process of producing such a delayed release pharmaceutical preparation.

Still another object of the present invention is to provide a method of administering orally such a delayed release pharmaceutical preparation.

Other objects of the present invention and advantageous features thereof will become apparent as the description proceeds.

In principle, the present invention is based on the discovery that only higher fatty acid triglycerides and especially triglycerides of higher fatty acids with 12 to 18 carbon atoms are needed for the delayed or timed release of the active agent. The preferred fatty acid triglycerides which have proved to be useful for the purpose of the present invention are glyceryl trimyristate, trilaurate, and tripalmitate. Addition of a water-soluble calcium salt is an essential feature of the present invention. Preferably small quantities of filler materials may also be incorporated as stabilizers into the preparation. In such a pharmaceutical preparation according to the present invention, hydrolysis of the carrier material, i.e., of the triglyceride is not effected, as in the known preparations, by an incorporated enzyme, but by the natural enzymes of the pancreatic juice. Hydrolysis, and hence the release, of the active agent are thus substantially confined to the duodenum and subsequent parts of the intestinal tract. The present preparations, therefore, have the great advantage over the known preparations that hydrolysis is not initiated immediately on contact with moisture, as this is the case with said known preparations.

According to one embodiment of the present invention there is provided a delayed release pharmaceutical preparation which comprises one or more pharmaceutically active agents, the delayed release of which in the intestinal tract of a patient is desired, one or more fatty acid triglycerides, a water-soluble calcium salt, and, if required, one or more physiologically inert filler materials.

The fatty acid triglyceride is preferably trilaurin, trimyristin, or tripalmitin, or a mixture of two or more thereof.

It is known (for instance, by PONOMAREFF, SOLIVA, and SPEISER, "Pharm.Acta Helv." vol. 43, page 158 (1968)) that the rate of lipase-catalyzed hydrolysis of glycerides decreases with increasing chain lengths of the fatty acids from 12 to 18 carbon atoms. It now transpires that under conditions in vitro which substantially agree with natural physiological conditions, trimyristin is particularly suitable in so far as the rate of hydrolysis is concerned.

The position of the ester bonds in different polymorphous forms of the triglycerides governs the ease of access by the lipase to these bonds so as to cause hydrolysis. For instance, the so-called $\alpha$-forms of the triglycerides are more rapidly hydrolyzed than the $\beta$- and $\beta'$-modifications, the packing density of the molecules, and the melting points rising in that order.

For selecting the best polymorphous form, the melting point is a matter of importance in connection with the stability of the respective crystal form during storage of the compounded preparation. Thus preferably the $\beta$-form of trilaurin (melting point of the $\alpha$-form: 15° C.; of the $\beta'$-form: 34.5° C; of the $\beta$-form: 46.5° C.), the $\beta'$- and particularly the $\beta$-form of trimyristin (melting point of the $\alpha$-form: 33° C.; of the $\beta'$-form: 46° C.; of the $\beta$-form: 58° C.), and the $\beta'$- and $\beta$-forms of tripalmitin (melting point of the $\alpha$-form: 45° C.; of the $\beta'$-form: 56.5° C.; of the $\beta$-form: 66° C.) are used in the present preparations. Optimum results are achieved when using the triglycerides in their $\beta$-form, because the speed of hydrolysis of such $\beta$-triglycerides is about the same and they are especially stable on storage.

It is, therefore, the preferred procedure to use the fatty acid glycerides in the $\beta$- or $\beta'$-modification.

The addition of a predetermined quantity of a water-soluble calcium salt which is at least equivalent to the quantity of esterified fatty acid present in the preparation, i.e., addition of at least 1½ moles of calcium ion for each mole of triglyceride, serves to precipitate, in the form of insoluble calcium soaps, the fatty acids which are set free by hydrolysis of the glycerides. As a result thereof the fatty acids are removed from the reaction equilibrium. Moreover, after administration, a viscous layer of the practically insoluble calcium soap rapidly envelopes the particles that are in the course of being hydrolyzed. Due thereto the speed of hydrolysis is slowed down. The quantity of the calcium salt contained in the preparation is supplemented by the calcium concentration of about 2 mval./l. which is physiologically present in the intestinal tract.

According to another embodiment of the present invention the method of producing the delayed release pharmaceutical preparation according to the present invention is characterized by the feature that the active agent or agents in mixture with the calcium salt and, if desired, with a filler material are suspended in the molten triglyceride or mixture of triglycerides and that spheres or granules of a grain size between about 100 $\mu$m. and about 1000 $\mu$m. and preferably between about 200 $\mu$m. and about 1000 $\mu$m. are formed from said suspension.

The addition of an inert filler material and/or stabilizer, such as fumed silica sold under the Trade Mark "Aerosil 200," serves to prevent active agents of high specific density from settling during formation of the suspension in the molten triglyceride before it solidifies.

Sedimentation of the active agent during formation of the suspension would result in a non-uniform distribution of the drug throughout the preparation and hence in a non-uniform rate of release. The pharmaceutically active agents that are suitable for the preparation according to the present invention are primarily of the kind which are absorbed by the organism through the intestines, and/or those of which it is desired that continuous absorption through the intestines should be spread over a prolonged period of time, such as 3 to 8 hours.

In the production of the pharmaceutical preparation according to the present invention the active agent or active agents together with the calcium salt or salts and, if required, filler material are preferably first reduced to a desired particle size by milling, for instance, in a ball mill, air jet mill, or the like, and are then mixed in the dry state.

As a matter of experience, it is advisable for the active agent to be in a micronized form with particles of a diameter from about 2 $\mu$m. to about 50 $\mu$m. and preferably from about 2 $\mu$m. to about 15 $\mu$m. with the major proportion being of a particle size of about 10 $\mu$m. On the other hand, it is the preferred procedure that the particles of the calcium salts are slightly coarser than those of the active agent. According to past experience it is desirable to comminute the calcium salts to particles of a diameter equal to about one-fifteenth of the size of the pellet forming the delayed release preparation according to the present invention, i.e., to a diameter preferably within the range of about 13 $\mu$m. to about 65 $\mu$m. The particle size of the other auxiliary substances, particularly of the fillers and stabilizers, should be very small, preferably less than about 10 $\mu$m.

The delayed release pharmaceutical preparation according to the present invention is preferably produced by proceeding as follows:

The triglyceride, or the triglycerides, are gently heated to a temperature above the melting point of the most stable modification, usually the $\beta$-modification. The mixture of solid components, i.e., calcium salts and pharmaceutically active agent is then introduced and is evenly and uniformly incorporated in the triglyceride melt with the aid of a high speed stirrer. The continuously agitated and tempered mixture is preferably allowed to solidify in finely dispersed form. This can be done either by a. atomizing the mixture with a high pressure atomizer and allowing it to solidify in a tempered air stream in free fall in a spray tower, this procedure resulting in the formation of small spheres from which the predetermined and desired particular grain size can be obtained by screening, or by b. forcing the mixture according to the method developed by LERK et al. (Pharm.Weekbl. vol. 106, page 141 (1971)) through a jet nozzle excited by high frequency to vibrate in vertical direction and then allowing the resultant droplets to solidify in free fall down a tube, this process permitting uniform particle sizes to be obtained, or by c. allowing the mixture to solidify in thin sheets on tempered plates, and then mechanically comminuting the sheets and recovering comminuted particles of the desired particle size by screening, a method which leads to the formation of a granular product of irregular shape.

The particle size of the pharmaceutically active agent determines the speed of hydrolysis or saponification. If large particles of the agent are incorporated into the spherical granules, formed from the triglyceride having embedded therein said agent, the surface of the triglyceride will undergo irregular deformation during saponification due to the detachment and/or dissolution of an exposed particle of the agent which, as a result of such dissolution, leaves a cavity enlarging the overall surface. This reduces the mechanical strength of the granules and results in an intermittent and discontinuous release of the active agent.

On the other hand, if the particle size of the active agent is too small in relation to the size of the pellet, particularly when the content of agent in the pellet is a high one, then the drug particles of the drug may mutually contact each other, with the result that channels are formed by the dissolution and/or detachment of said drug particles. Thus, finally, a spongy, only slowly hydrolyzing mass or matrix of triglyceride remains from which the agent is released at a rate that no longer depends upon the speed of hydrolysis.

The grain size of the pellets or granules is preferably between about 200 $\mu$m. and about 1000 $\mu$m., and the ratio of the particle size of the active agent to the size of the pellets is preferably between about 1 : 20 and about 1 : 100. A content of about 1% to about 50% and preferably of about 5% to about 26% of pharmaceutically active agent in the pellets provides a satisfactory and uniform rate of release during a prolonged period of time.

The proportion of the therapeutically active agent and calcium salt to fatty acid triglyceride in the preparation may be between about 5% and about 30% by volume.

DESCRIPTION OF THE PREFERRED EMBODIMENT

The present invention will be illustrated more in detail by the following Examples in which all parts and percentages are parts and percentages by weight unless otherwise specified.

EXAMPLE 1

For the preparation of a matrix formulation for the delayed release of sulfanilamide from a pharmaceutical preparation consisting of said sulfanilamide, glyceryl trimyristate, calcium levulinate (Ph.Helv.VI), and fumed silica of the "Aerosil 200" type, the sulfanilamide is first comminuted to a particle size between 5 $\mu$m. and 20 $\mu$m. and the calcium salt to an average particle size between 5 $\mu$m. and 65 $\mu$m. 10 parts of sulfanilamide, 16 parts of comminuted calcium levulinate, and 1 part of fumed silica are then mixed homogeneously. The resulting mixture of said solid particles is dispersed homogeneously at 70° C. in 75 parts of $\beta$-glyceryl trimyristate or a mixture of higher fatty acid triglycerides.

To prepare granules from the resulting mixture, it is continuously stirred by means of a stirrer and is poured on and distributed in the form of a 2 mm. thick layer over a cold metal plate coated with polytetrafluoro ethylene. Said plate is kept as 0° C. and thus causes the mixture to solidify. The thus obtained solidified layer is comminuted in a slowly revolving milling device to avoid heat generation. Granules of the desired grain size, for instance, of a diameter between 400 μm. and 600 μm. are obtained by screening.

In a similar manner there can be produced spherical pellets of a predetermined grain size by the method of LERK et al. (Pharm. Weekbl. vol. 106, page 149 (1971)) by atomizing and causing solidification of the molten mixture after determination of its density, viscosity, and surface tension of the molten mixture.

For producing a ready-to-use pharmaceutical preparation the resulting pellets or granules either are
a. filled as such, for instance, into divided capsules of hardened gelatin, or are
b. compressed at a low pressure into tablets on a slow-running tabletting machine after addition of a hydrophilic opening agent, or are
c. suspended in an aqueous medium after addition of viscosity-increasing substances, such as mucilages, aromatic substances, and other aids, such as peptizing agents.

In order to produce a substantial initial pharmaceutical effect, there can be added an initial dose of sulfanilamide but in non-pelletized form, i.e., not embedded in the triglyceride, to the above gelatin capsules, tablets, or aqueous preparations.

After oral administration the hardened gelatin capsule is dissolved in the stomach whereby the initial, non-embedded sulfanilamide dose becomes immediately available while the embedded part of the sulfanilamide is gradually and uniformly released in the intestines.

EXAMPLE 2

A homogeneous powder mixture consisting of 11 parts of micronized sulfanilamide of an average particle size of 10 μm. and 0.5 parts of colloidal silica is uniformly distributed at 70° C. in 30 parts of molten β-glyceryl tripalmitate. Spherical pellets of an average diameter of 500 μm. (Mixture 1) are obtained therefrom by atomization and solidification.

A suspension of 16 parts of calcium levulinate and 0.5 parts of colloidal silica in 43 parts of molten β-glyceryl tripalmitate is separately pelletized by atomization with the formation of pellets having an average diameter of 500 μm. (Mixture 2). 59 parts of Mixture 1 and 40 parts of Mixture 2 are homogeneously mixed with each other and are filled into two-part capsules made of hardened gelatin so that each capsule contains a dose of 250 mg. of sulfanilamide. Thereafter, 100 mg. of sulfanilamide of a particle size between 50 μm. and 150 μm. which are not enveloped by the triglyceride are filled into the capsules. These particles of sulfanilamide are made available to the body immediately after the hardened gelatin capsule has been dissolved in the stomach. It represents the so-called initial dose of sulfanilamide. In contrast thereto the triglyceride-enveloped sulfanilamide can exert its therapeutic action only when it has passed into the intestines. In this manner it is possible to produce a rather quick and strong but short-time, initial therapeutic effect while the drug enveloped in the triglyceride is only slowly released over a prolonged period of time.

EXAMPLE 3

10 parts of a finely divided tripelennamine hydrochloride of an average particle size of 10 μm., 1 part of colloidal silica, and 14 parts of calcium gluconate of an average particle size of 50 μm. are suspended at 70° C. in 75 parts of molten β-glyceryl trimyristate. The homogeneous suspension is solidified by pouring it on a poly-tetrafluoro ethylene-coated cold metal plate to form layers of 2 mm. thickness. The cooled and solidified layers are comminuted to a grain size of about 600 μm. by granulation and screening in the cold. 10 parts of tripelennamine citrate of an average particle size of 110 μm., 5 parts of marantha starch, 5 parts of the finely divided cellulose powder sold under the Trade Mark "AVICEL," and 1 part of a mixture of 90% of talcum and 10% of magnesium stearate are then mixed homogeneously with the triglyceride-embedded drug. The resulting granular composition is then compressed on a slow running tabletting machine to form tablets, each containing 100 mg. of tripelennamine.

EXAMPLE 4

10 parts of finely divided glutethimide of an average particle size of 6 μm. and 0.6 parts of colloidal silica are suspended in 40 parts of molten glyceryl trilaurate. The mixture is pelletized by atomizing it so as to form pellets of an average particle size of 200 μm. In the same manner 14 parts of calcium levulinate of an average particle size of 20 μm., 0.4 parts of colloidal silica, and 35 parts of glyceryl trilaurate are separately pelletized. The pellets containing the glutethimide and the calcium levulinate-containing pellets are intimately mixed in the above stated quantitative proportions.

0.9 parts of sodium carboxy methyl cellulose (viscosity: 1300 cps. to 2200 cps. at 25° C. in 1% solution) are caused to swell in 60 parts of cold water while stirring. 0.078 parts of methyl p-hydroxy benzoate, 0.042 parts of propyl p-hydroxy benzoate and 38 parts of saccharose are completely dissolved therein at about 90° C. Into the resulting cooled mucilaginous solution there is introduced a mixture of aromatic agents consisting of 0.06 parts of citric acid, 0.002 parts of lemon oil, if desired, other fruit essences, and 0.0025 parts of polyhydroxy ethylene sorbitane monolaurate in 1 part of water. 25 parts of the pelletized glutethimide and calcium levulinate-containing mixture are carefully incorporated into the resulting cooled hydrosol of sodium carboxy methyl cellulose. After gentle homogenization, the resulting sol is made up with water to yield 125 parts of a syrup having the drug suspended therein.

In place of glyceryl trimyristate, glyceryl tripalmitate, or glyceryl trilaurate as used in the preceding examples, there can also be employed corresponding amounts of a mixture of said triglycerides and also the triglycerides of other higher fatty acids such as glyceryl tristearate, i.e., in general the triglycerides of higher fatty acids having 12 and 18 carbon atoms.

In place of calcium levulinate and calcium gluconate as used in the preceding examples, there can also be employed, for instance, calcium citrate, calcium chloride, and other water-soluble, physiologically inert calcium salts.

In place of colloidal silica and fumed silica there can be used other non-toxic filler materials, such as calcium oxide, calcium carbonate, various types of clay, other types of microcrystalline cellulose than that known under the Trade Mark "AVICEL," lactose, and others.

Useful antoxydants are, for instance, butyl hydroxy anisol, cysteine, hydroquinone, pyrogallol, pyrocatechol, quinones, and others.

In place of methyl p-hydroxy benzoate and propyl p-hydroxy benzoate, there can be used as preserving agents other p-hydroxy benzoic acid esters, benzoic acid, sorbic acid, and the like physiologically compatible preserving agents.

Other hydrophilic disintegrating aids than those used in the preceding examples can be added such as potato starch, rye starch, corn starch, wheat starch, agar, pectin, cellulose derivatives, saccharose, and the like.

As pointed out hereinabove, the preferred form of the tri-glycerides is the β-form because it is the most stable form. It is, therefore, advisable, especially when using mixtures of the claimed triglycerides, to use them in the β-form in order to achieve the same speed of hydrolysis and stability on storage.

The amount of calcium salt added must correspond to at least one third of a mole of calcium ions for each mole of triglyceride. Of course, larger amounts of calcium salt can also be added. Under certain conditions the calcium salt addition may be omitted completely because, as explained hereinabove, the calcium ion concentration which is physiologically present in the intestines is frequently sufficient to cause formation of the calcium soap enveloping the particles of active agent.

The amounts of the therapeutically active agent can also be varied. They may be between about 1% and about 50% of the preparation depending upon the specific agent used.

In place of the active agent used in the preceding examples, namely in place of sulfanilamide, tripelennamine hydrochloride, or glutethimide, there may be used other orally administrable therapeutically effective agents. Such agents are, for instance, other sulfonamides such as sulfathiazole, sulfacarbamide, sulfisomidine, sulfaguanidine, sulfamethoxazole, and others;

analgesic agents such as acetyl salicylic acid, acetanilide, acetophenetidine, antipyrine, phenylbutazone, meperidine, methadone, and others;

antihistaminic agents such as pheniramine, diphenhydramine, promethazine, chloropromazine, and others;

sedative and hypnotica such as the various barbiturates, for instance, barbital, phenobarbital, cyclobarbital, and the like;

psychotropic agents such as diazepine compounds, carbamic acid esters, phenothiazine compounds, and the like;

antitubercular agents such as isoniazid, and the like;

antimalaria agents such as chloroquine, primaquine, and the like;

antibiotics such as the tetracyclines, penicillin, streptomycin, and the like;

hypertensive agents such as reserpine, syrosingopine, and the like;

hypoglycemic agents such as tolbutamide, chlorpropamide, and the like, and many other therapeutically active agents which can be orally administered and of which a delayed or timed release action is desired.

I claim:

1. A delayed release pharmaceutical preparation in granular form comprising intermixed particles of at least one orally administrable therapeutically active agent and a substantially non-toxic water-soluble calcium salt selected from the group consisting of calcium levulinate, calcium gluconate, calcium citrate and calcium chloride, at least part of said particles of said agent and said salt being enveloped by solidifying a melt of at least one triglyceride of a fatty acid of 12 to 18 carbon atoms, said salt being present in an amount to provide at least 1½ moles of calcium ion for each mole of said triglyceride and forming a substantially insoluble calcium soap with the fatty acid produced upon hydrolysis of said triglyceride in the intestinal tract, the granules of said preparation being of a grain size between about 0.1 mm. and about 1.0 mm. and containing between about 1 and 50% of said agent.

2. The pharmaceutical preparation of claim 1, wherein the triglyceride is selected from the group consisting of trilaurin, trimyristin, tripalmitin, and mixtures of said triglycerides.

3. The pharmaceutical preparation of claim 1, wherein the fatty acid triglyceride is present in the form of its β-modification.

4. The pharmaceutical preparation of claim 1, wherein the proportion of therapeutically active agent and calcium salt to fatty acid triglyceride in the preparation is between about 5% and about 30% by volume.

5. The pharmaceutical preparation of claim 1, wherein the preparation is in the form of spherical pellets of a diameter between about 0.1 mm. and about 1 mm. and wherein the ratio of the particle size of the active agent to the size of the pellet is between about 1 : 20 and about 1 : 100.

6. The pharmaceutical preparation of claim 1, additionally containing physiologically inert filler materials.

7. The pharmaceutical preparation of claim 1, additionally containing physiologically inert filler materials, preserving agents, stabilizers, aroma imparting and taste improving agents, and disintegration promoting agents.

8. A delayed release pharmaceutical composition having the preparation of claim 1 enclosed in a gelatin capsule.

9. A delayed release pharmaceutical composition in readily disintegrating tablet form containing the preparation of claim 1 and conventional tabletting adjuvants.

10. A delayed release pharmaceutical composition in aqueous dispersion form containing the granules of the preparation of claim 1 suspended in an aqueous medium containing a physiologically compatible, viscosity increasing agent.

* * * * *